US007022288B1

(12) United States Patent
Boss

(10) Patent No.: US 7,022,288 B1
(45) Date of Patent: Apr. 4, 2006

(54) CHEMICAL DETECTION SENSOR SYSTEM

(75) Inventor: Pamela Boss, San Diego, CA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 508 days.

(21) Appl. No.: 10/294,655

(22) Filed: Nov. 13, 2002

(51) Int. Cl.
- G01N 21/01 (2006.01)
- G01N 27/27 (2006.01)
- G01N 33/00 (2006.01)

(52) U.S. Cl. ............... 422/82.05; 356/301; 422/68.1; 422/82.01; 422/82.02; 422/82.06; 436/149; 436/150; 436/151; 436/164; 436/167; 436/181

(58) Field of Classification Search ............... 356/301; 422/68.1, 82.01–82.02, 82.05–82.06; 436/86, 436/91–93, 96, 98, 104, 107, 110, 120, 124, 436/128–135, 139–142, 147, 164, 149–151, 436/167, 181
See application file for complete search history.

(56) References Cited

U.S. PATENT DOCUMENTS

| | | | |
|---|---|---|---|
| 4,781,458 A | 11/1988 | Angel et al. | |
| 5,010,776 A | 4/1991 | Lucero et al. | |
| 5,112,127 A | 5/1992 | Carrabba et al. | |
| 5,194,913 A | 3/1993 | Myrick et al. | |
| 5,241,368 A | 8/1993 | Ponstingl et al. | |
| 5,255,067 A * | 10/1993 | Carrabba et al. | 356/301 |
| 5,327,211 A * | 7/1994 | Carron et al. | 356/301 |
| 5,376,556 A | 12/1994 | Tarcha et al. | |
| 5,402,508 A | 3/1995 | O'Rourke et al. | |
| 5,721,102 A * | 2/1998 | Vo-Dinh | 435/6 |
| 5,739,536 A | 4/1998 | Bucholtz et al. | |
| 5,759,859 A | 6/1998 | Sausa | |
| 5,774,610 A | 6/1998 | O'Rourke et al. | |
| 5,814,516 A * | 9/1998 | Vo-Dinh | 435/287.2 |
| 5,864,397 A | 1/1999 | Vo-Dinh | |
| 6,018,389 A | 1/2000 | Kyle et al. | |
| 6,028,666 A | 2/2000 | Boss et al. | |
| 6,040,191 A * | 3/2000 | Grow | 436/172 |
| 6,406,777 B1 | 6/2002 | Boss et al. | |
| 6,558,956 B1 * | 5/2003 | Carron et al. | 436/86 |
| 6,614,523 B1 * | 9/2003 | Boss et al. | 356/301 |
| 6,649,683 B1 * | 11/2003 | Bell | 524/440 |
| 6,743,581 B1 * | 6/2004 | Vo-Dinh | 435/6 |
| 6,750,065 B1 * | 6/2004 | White et al. | 436/518 |

OTHER PUBLICATIONS

Carron, K. et al, Environmental Science andTechnology 1992, 26, 1950-1954.*

(Continued)

Primary Examiner—Arlen Soderquist
(74) Attorney, Agent, or Firm—Michael A. Kagan; Peter A. Lipovsky; Allan Y. Lee

(57) ABSTRACT

A chemical detection sensor system comprises a support structure; multiple SERS chemical detection sensors supported by the support structure; multiple chemical reaction sensors, wherein each of the chemical reaction sensors is disposed for undergoing a state change in response to an occurrence of a chemical reaction at one of the SERS chemical detection sensors; a processor supported by the support structure for recording data representing occurrence of a chemical reaction at any of the chemical detection sensors in response to sensing the state change; and a power source for energizing the processor.

23 Claims, 20 Drawing Sheets

OTHER PUBLICATIONS

Carrabba, M. M. et al, Proceedings—Electrochemical Society 1993, 93-7, 634-642.*
Crane, L. G. et al, Analytical Chemistry 1995, 67, 360-634.*
Carron, K. T. et al, Analytical Chemistry 1995, 67, 3353-3356.*
Lee, Y.-H. et al, SPIE 1999, 3857, 76-84.*
Ehler, T. T. et al, Journal of Physical Chemistry B 1997, 101, 3174-3180.*
Yonzon, C. R. et al, SPIE 2003, 5224, 78-85.*

Storey, J.M.E et al, Electrochemical SERS Detection of Chlorinated Hydrocarbons in Aquenous Solutions, vol. 48, No. 10, 1994 Applied Spectrocopy, 1265-1271.
Adsorption of Chlorinated Ethylenes at 1-Octadecanethiol-Modified Silver Surfaces, Analytical Chemistry, vol. 66, No. 4 Feb. 15, 1994, Mullen, K. et al, 478-483.
Long fiber-optic remote Raman probe for detection and identification of weak scatterers, Dec. 20, 1992/vol. 31, No. 36/ Applied Optics, Schoen, C.L. et al, 7707-7715.

* cited by examiner

US 7,022,288 B1

CHEMICAL DETECTION SENSOR SYSTEM

BACKGROUND OF THE INVENTION

In the 1970s, it was discovered that Raman scattering of analyte molecules, upon irradiation with optical energy, can be enhanced as much as $10^6$ to $10^7$ when the molecules are adsorbed on noble metals such as silver, copper, and gold. This phenomenon is known as surface enhanced Raman spectroscopy (SERS). A SERS structure generally includes a metal layer formed on a substrate and is used to detect the presence of an analyte by examining the emissions from the substrate when irradiated with optical energy. SERS emissions, or spectra, have been used to detect and identify trace organics and as a detection method in gas chromatography, liquid chromatography, and thin layer chromatography. Electro chemical SERS and SERS of chemically modified surfaces have been used to detect aromatic compounds and chlorinated hydrocarbons and other organic contaminants of environmental concern in the ppb to ppm range. SERS analysis generally requires bulky equipment and typically is performed in a laboratory setting. However, there are many applications in which it would be desirable to detect the presence of analytes in other than laboratory environments. A SERS sensor that is easily transportable and that may be used in the field would be desirable.

SUMMARY OF THE INVENTION

A chemical detection sensor system comprises a support structure; multiple SERS chemical detection sensors mounted on the support structure; multiple chemical reaction sensors, wherein each of the chemical reaction sensors undergoes a state change in response to an occurrence of a chemical reaction at one of the SERS chemical detection sensors; a processor supported by the support structure for recording data representing the occurrence of a chemical reaction at any of the chemical detection sensors in response to sensing the state change; and a power source for energizing the processor.

BRIEF DESCRIPTION OF THE DRAWINGS

Throughout the several views, like elements are referenced using like references.

DESCRIPTION OF THE PREFERRED EMBODIMENT

An embodiment of a chemical detection sensor system includes multiple SERS chemical detection sensors that may be configured into an array. Each chemical detection sensor of the array is designed to react with a specific class of compounds and consists of a thiol-coated, SERS-active substrate. Thiol coatings are chosen that will chemically bond to an analyte that one is interested in detecting. Once an analyte binds to the thiol coating, the analyte may be identified and quantified by its characteristic Raman emissions. Thus, an array of SERS chemical detection sensors may be designed to detect one or more different classes of chemicals or analytes, depending upon the specific thiol coating employed.

Figure 1:
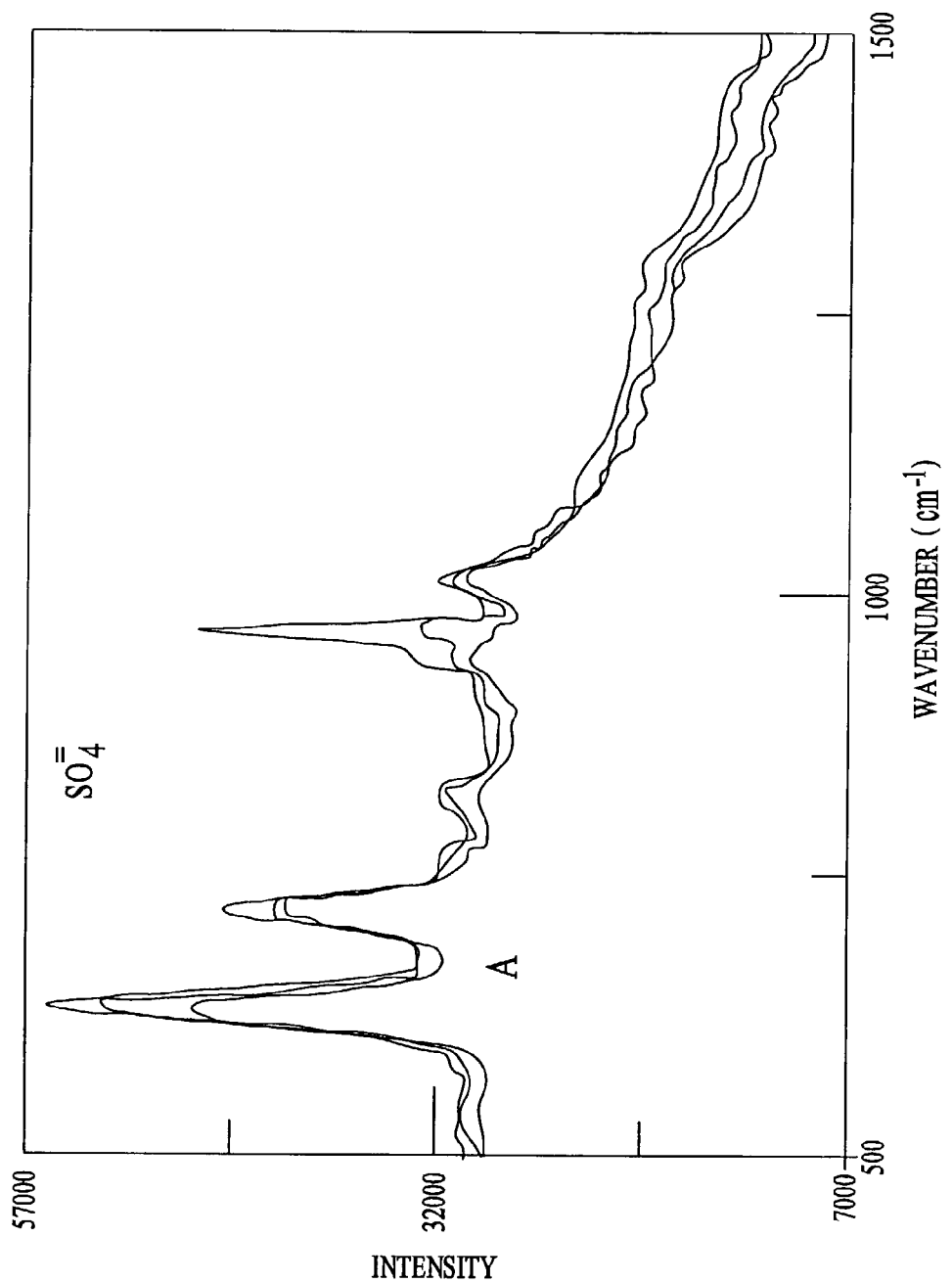
FIG. 1 shows SERS spectra of a sulfate interaction with an embodiment of a cysteamine coated SERS chemical detection sensor.
Figure 2:
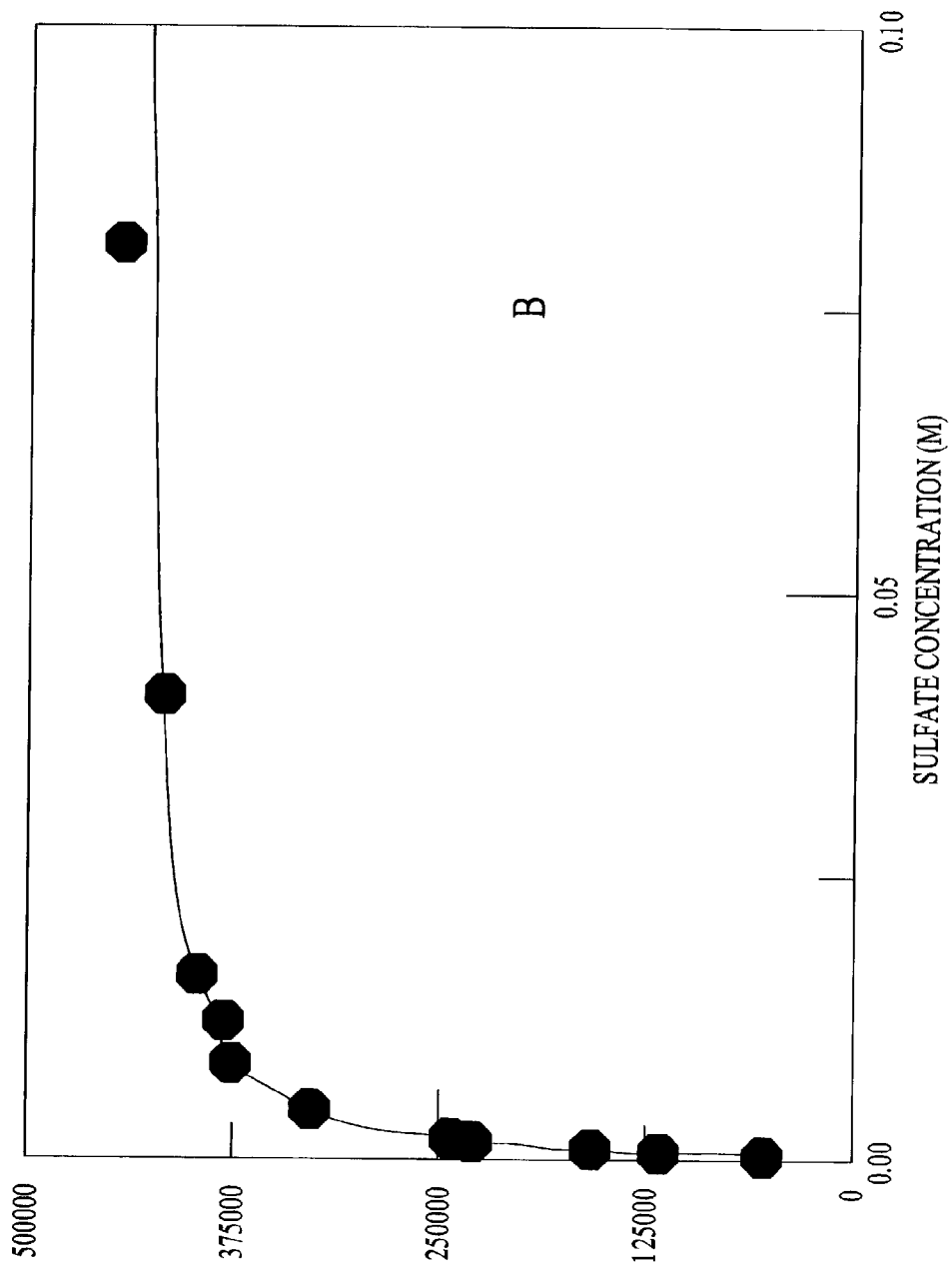
FIG. 2 shows the concentration of the sulfate represented in FIG. 1.

An example of an expected spectral response is shown in FIG. 1, which shows SERS spectra of sulfate interaction with a cysteamine coated chemical detection sensor. Cysteamine has a quaternary ammonium group that forms an ion pair with sulfate ion. In the example described herein, the sulfate compound is the analyte. In FIG. 1, the evolution of the sulfate peak as it interacts with the coating is seen at a wavelength of about 1000 cm$^{-1}$. The concentration response of the sulfate, shown in FIG. 2, may be used to quantify the amount of sulfate that reacted with the chemical detection sensor. In the example shown in FIG. 1, the cysteamine coating reacts reversibly with sulfate ion. It is desirable for the analyte to irreversibly chemically react with the coating on the chemical detection sensor so as to form a new compound, that may be detected and quantified by its characteristic Raman spectral emission.

The thiol coating on a SERS chemical detection sensor protects the SERS-active metal surface of the sensor from degradation due to oxidation. However, depending upon the thiol coating selected, the chemical detection sensor may be employed to detect chemicals of environmental concern such as: drugs, explosives, and agents used in chemical warfare. Because many chemical reactions occur in water, one or more of the chemical detection sensors may include a hydrogel layer to allow the thiol coating to chemically react with specific analytes. The hydrogel layer may be formulated to contain the needed reagents to facilitate reaction between the analyte and the thiol coating.

Each SERS chemical detection sensor is intended for a single use application. The chemical detection sensor system may be carried by a person who is conducting site inspections, left in a given area for a specified period of time, or mounted on a remotely operated vehicle such as a car, airplane, or robot. After exposure, the chemical detection sensor system may be taken into a laboratory where the individual SERS chemical detection sensors may be individually interrogated using a Raman-based spectroscopy system to identify the chemicals that have reacted with the thiol coatings of the various SERS chemical detection sensors. Interrogation of only those SERS chemical detection sensors that have undergone a chemical reaction may be determined by coupling a SERS chemical detection sensor to a particular chemical reaction sensor of the sensor array. If a chemical reaction occurs, the chemical reaction sensor associated with a specific SERS chemical detection sensor undergoes a state change that is indicative of a chemical reaction.

Figure 3A:
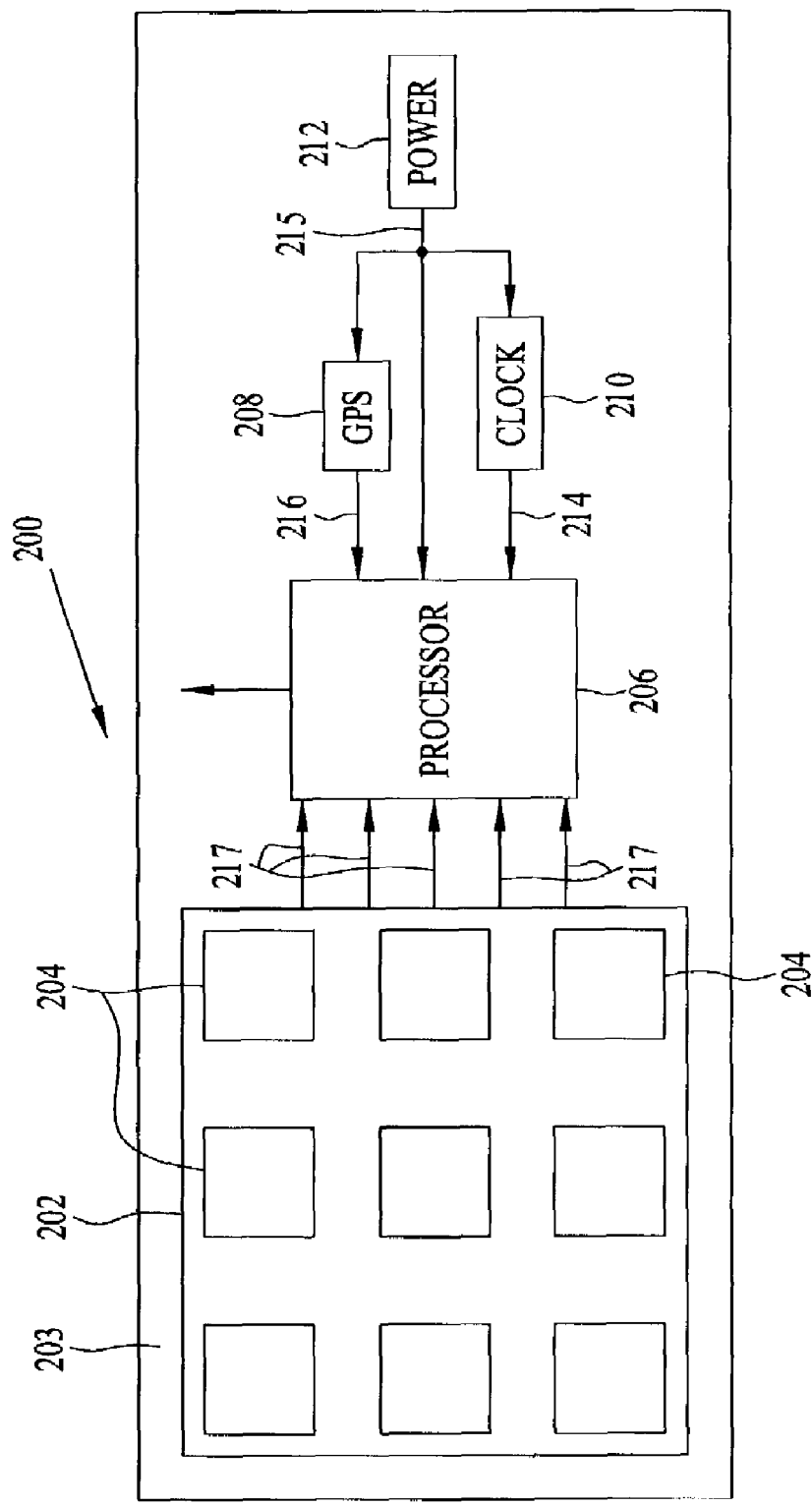
FIGS. 3A and 3B show an embodiment of a chemical detection sensor system having multiple SERS chemical detection sensors.
Figure 3B:
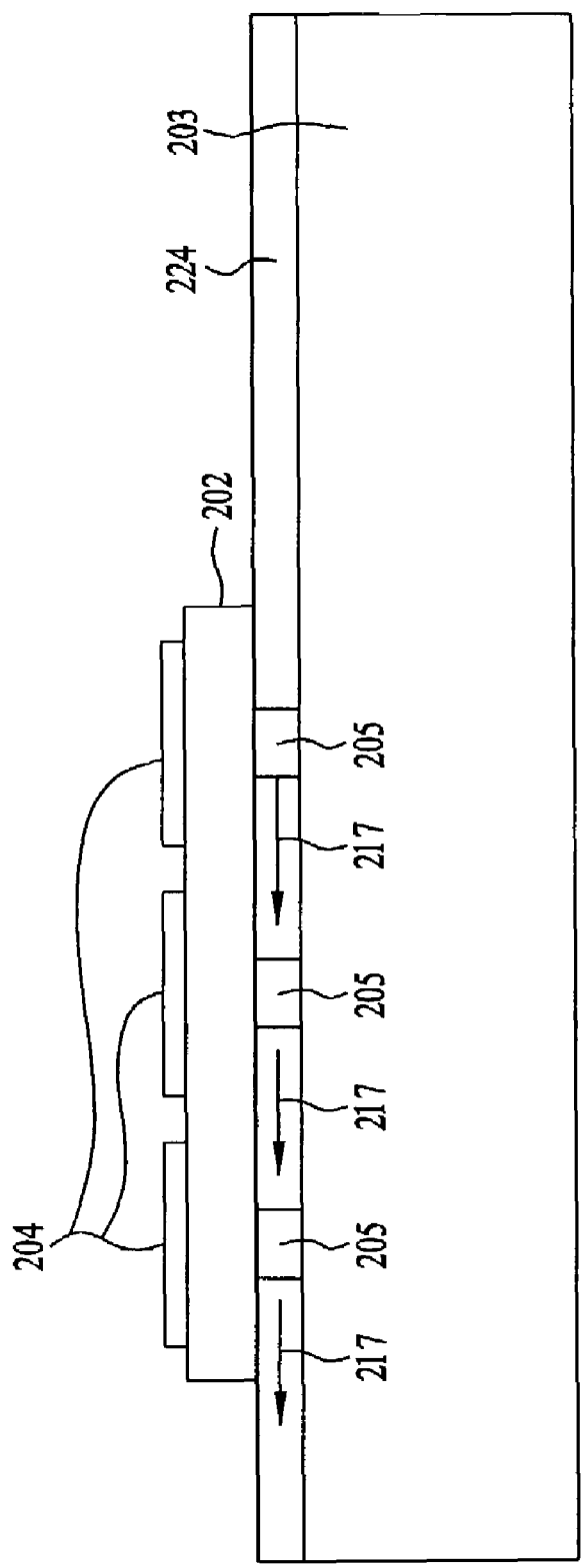

Referring to FIGS. 3A and 3B, there is shown a surface enhanced Raman spectroscopy chemical detection sensor system 200 for detecting chemicals of interest, wherein such chemicals may also be referenced herein as analytes. Chemical detection sensor system 200 includes a support structure 203, such as a printed circuit board; a module 202 that houses an array of SERS chemical detection sensors and is supported by the structure 203; multiple chemical reaction sensors 205; processor 206; optional global positioning system (GPS) 208; optional clock 210; and power source 212, all or some of which may be supported by structure 203. Power source 212 provides electrical power to each of global positioning system (GPS) 208, clock 210, and processor 206 via power line 215. Each individual chemical reaction sensors 205 may be mounted in a fixing layer 224 formed on support structure 203. For example, fixing layer 224 may be formed of an epoxy, or any other substance typically used for affixing electrical components to a support structure. Chemical reaction sensors 205 are positioned in fixing layer 224 which is mounted between module 202 and support structure 203. Each chemical reaction sensor 205 is disposed to detect a change in state when the specific SERS chemical detection sensor 204 undergoes a chemical reaction with the analyte. State changes for each sensor 205 are presented on a signal line 217 coupled between each SERS chemical detection sensor 204 and processor 206. By way of example, chemical reaction sensor 205 may be implemented as a thermocouple and/or a surface acoustic wave (SAW) device. When implemented as a thermocouple, chemical reaction sensor 205 is disposed for detecting the heat transfer either to or from the SERS chemical detection sensor 204 that is operably coupled to that particular chemical reaction sensor 205. The heat transfer is caused by a chemical reaction between the SERS chemical detection sensor 204 and an analyte. When implemented as a SAW device, chemical reaction sensor 205 detects changes in the acoustic properties of a particular SERS chemical detection sensor 204 caused by a chemical reaction between the SERS chemical detection sensor and an analyte. Then processor 206 records an occurrence of a chemical reaction at one or more of the SERS chemical detection sensors 204, based on sensing the state change that is detectable on one of the signal lines 217. Optionally, processor 206 may also record the specific time and/or position of the sensor 200 based on clock signal 214 generated by clock 210, and global position signal 216 generated by GPS 208 in order to determine the time and location of the occurrence of particular chemical reactions detected by sensor 200. The clock signal 214 represents a time value generated by clock 210, and global position signal 216 represents a global position value generated by GPS 208.

Figure 4:
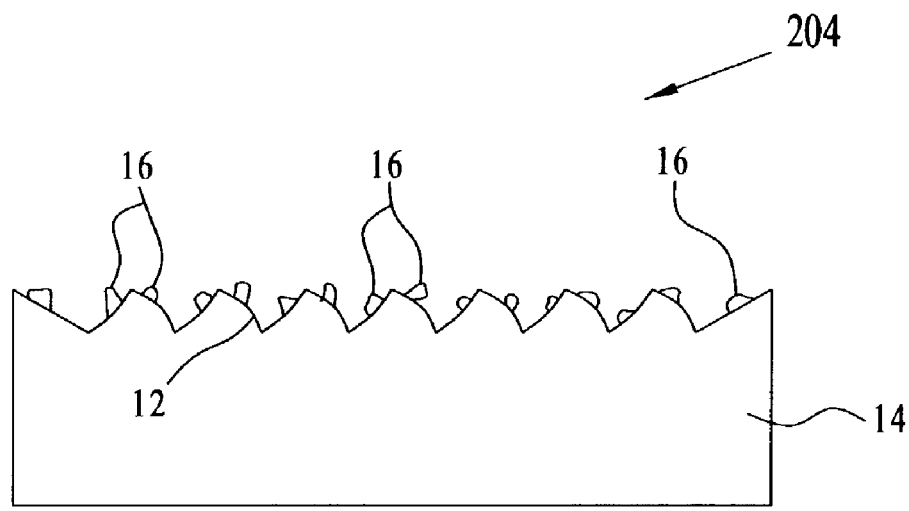
FIG. 4 is a cross-sectional view of an embodiment of a SERS chemical detection sensor.
Figure 5:
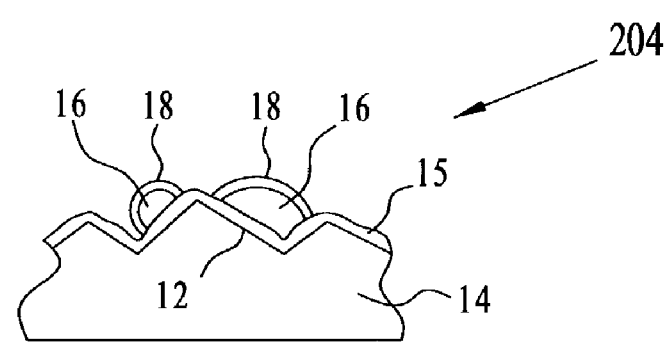
FIG. 5 is an enlarged view of a section of the SERS chemical detection sensor depicted in FIG. 4.

The manufacture of a SERS chemical detection sensor 204 includes metal islands formed on the roughened surface of a transparent substrate such as transparent glass. When in contact with an analyte of interest and illuminated with appropriate excitation energy, a SERS chemical detection sensor will produce spectra having unique characteristics that are used to identify and quantify the amount of analyte detected. By way of example, analytes may include organic, metallic, and anionic contaminants. Referring to FIGS. 4 and 5, SERS chemical detection sensor 204 includes a specially roughened surface 12 of a transparent substrate 14, such as glass, on which an adhesion layer 15 is formed. Adhesion layer 15 promotes the bonding of the metal islands 16 to the glass substrate 14. The metal islands 16 are formed, as for example, by vapor deposition, on adhesion layer 15 to create a metal patterned substrate 11, shown in FIG. 8. A thiol coating, or self-assembled monolayer 18 on metal islands 16 protects metal islands 16 from degradation, thereby extending the lifetime of chemical detection sensor 204 when exposed to air or aqueous environments from minutes or hours to months. The roughened surface 12 facilitates both a good SERS response and adhesion of the metal islands 16 to the substrate 14.

In the fabrication of SERS chemical detection sensor 204, transparent substrate 14, such as a clear borosilicate glass slide, is carefully cleaned and prepared prior to having a metal film deposited on it. First, substrate 14 is immersed in a heated or boiling liquid reagent or reagents to remove any oils, metallic materials, and other contaminants that may be present on substrate 14. By way of example, a transparent substrate 14 may be immersed in boiling nitric acid for about 30 minutes. However, other liquid reagents also may be used such as hydrofluoric acid, hydrochloric acid, potassium hydroxide. Next, substrate 14 is removed from the boiling nitric acid and rinsed in either deionized or distilled water. After the water rinse, substrate 14 is immersed in hot or boiling methanol for about 30 minutes, followed by immersion in boiling acetone for about 30 minutes. This procedure removes any remaining organic contaminants. Substrate 14 is then removed from the methanol and allowed to air dry, as for example, about 1 hour.

Figure 6:
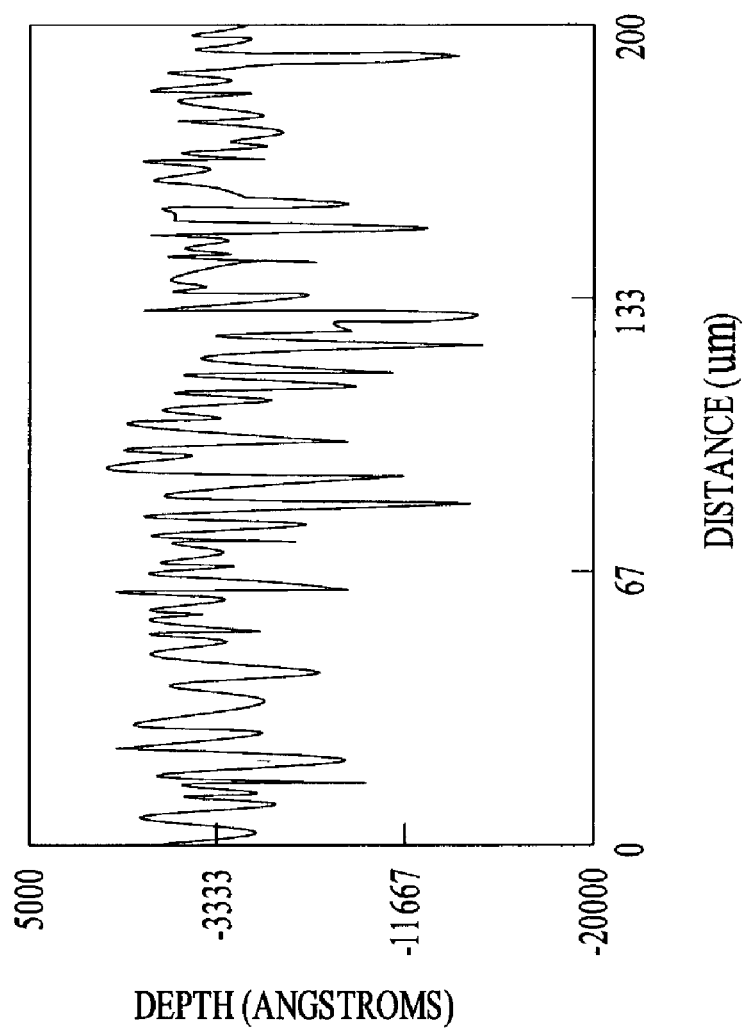
FIG. 6 is a surface profile of the roughened surface of the substrate used in the SERS chemical detection sensor of FIG. 4.

Referring to FIG. 6, cleaned surface 12 of substrate 14 is etched to provide surface 12 with a surface roughness having a maximum peak to valley depth of about 16,000, an average peak to valley depth of about 2,500, and a peak-to-peak periodicity of about 12.5 microns. The roughness of surface 12 and its periodicity may be measured using a Dektak³ST Surface Profiler (Vecco Sloan Technology). In contrast, commercial white glass generally has a surface having a peak to valley depth of about 200,000, an average peak to valley depth of about 43,700, and a peak-to-peak periodicity of about 100 microns. The combination of surface roughness and peak-to-peak periodicity of surface 12 provides SERS chemical detection sensor 204 with a greatly enhanced SERS response. In one implementation of an embodiment of a SERS chemical detection sensor 204, surface 12 may be etched using a chemical etchant such as an HF based cream such as Velvet Etching Cream, manufactured by McKay International. Experience has shown that etching white glass for approximately 1 minute provides the surface roughness characteristics described above. Alternatively, surface 12 may be roughened using standard photo lithographic techniques.

Figure 7:
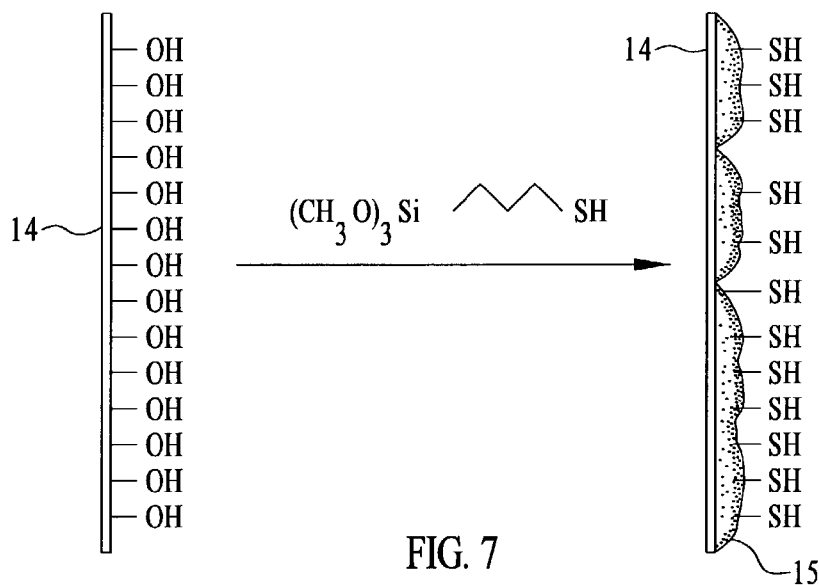
FIG. 7 represents the formation of a silane layer on surface of a glass substrate used in an embodiment of a SERS chemical detection sensor.

After etching, structure 14 is rinsed with distilled or deionized water, followed by an ethanol rinse. The cleaned, etched substrate 14 is then derivitized in a silanization agent such as a 1:10 mixture by volume of (3-mercaptopropyl) trimethoxysilane (MCTMS) in ethanol for about 24 hours to form adhesion layer 15 on roughened surface 12. As shown in FIG. 7, it is believed that the derivitization process causes a silane layer to bond to ⁻OH functional groups believed to be present on surface 12 when substrate 14 is implemented as a transparent glass substrate. Substrate 14 was next rinsed in ethanol to remove unreacted (3-mercaptopropyl) trimethoxysilane and allowed to air dry. Adhesion layer 15 promotes bonding between roughened surface 12 and metal islands 16.

Figure 12:
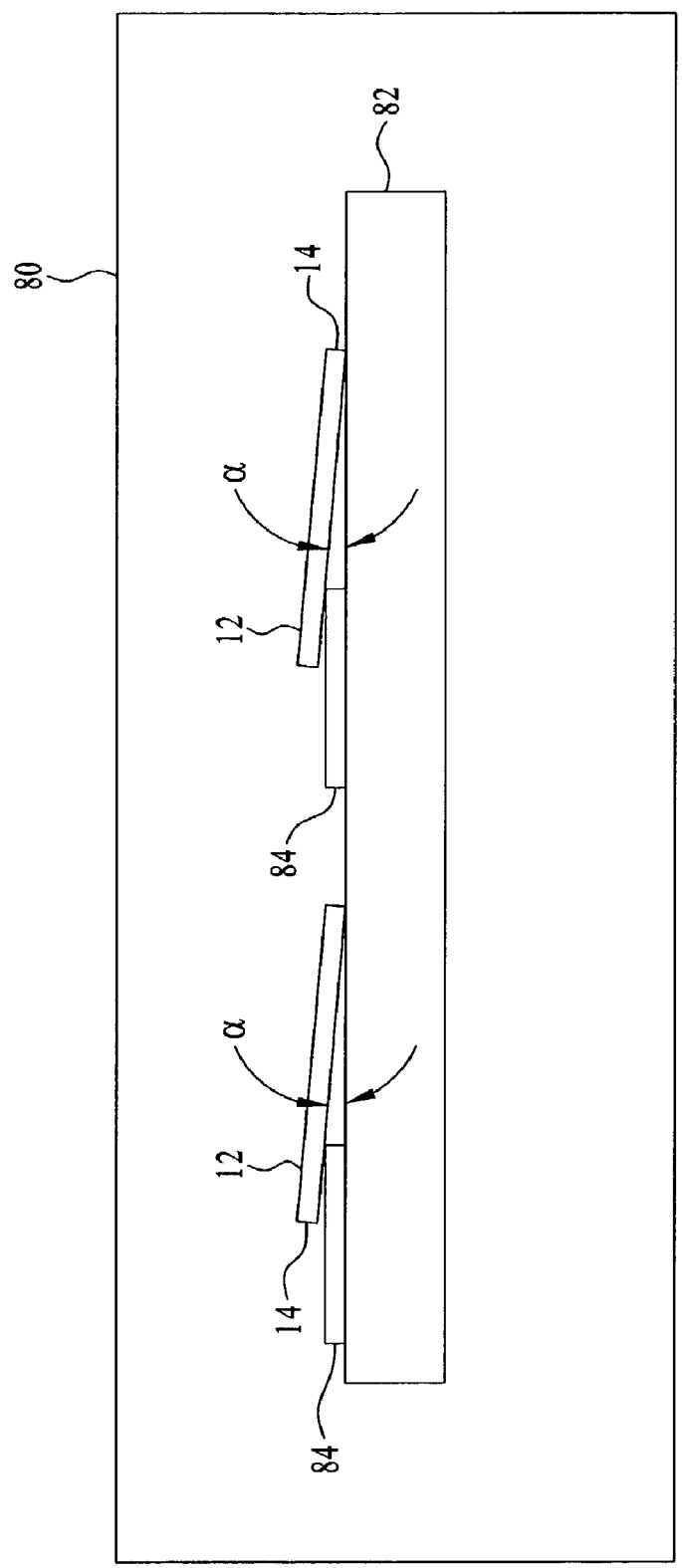
FIG. 12 shows glass substrates mounted at an angle in a vapor deposition system in the manufacture of an embodiment of a SERS chemical detection sensor.

When metal islands 16 are formed by vapor deposition, as shown in FIG. 12, one or more cleaned substrates 14 are positioned so that they each rest on both a stainless steel spacer 84 and on support structure 82 in a vapor deposition system 80 so that roughened surfaces 12 face upwardly at a slight angle a with respect to the horizontal. The angle may be in the range, for example, of about 3–5 degrees, and more preferably, 4.5 degrees. The purpose of canting substrate 14 at an angle with respect to the horizontal is to create "shadows" that prevent the deposited metal that comprises metal islands 16 from forming a continuous metal layer on roughened or discontinuous surface 12. Discontinuities on the surfaces of metal islands 16 have that have been shown to enhance the SERS response of SERS chemical detection sensor 204. By way of example, a metal such as gold, silver, or copper may be vapor deposited onto adhesion layer 15 to form metal islands 16. In one implementation of an embodiment of chemical detection sensor 204, gold islands were vapor deposited onto roughened surface 12 using material evaporated from an Aldrich, 99.99% pure gold wire. Vapor deposition system 80 may be implemented as a Vecco Model E.C. 200 vapor deposition system. As a result of the aforesaid processing, adhesion layer 15 durably bonds metal islands 16 to roughened surface 12 so that SERS chemical detection sensor 204 may provide an effective SERS response after being immersed in an aqueous environment for months.

Figure 8:
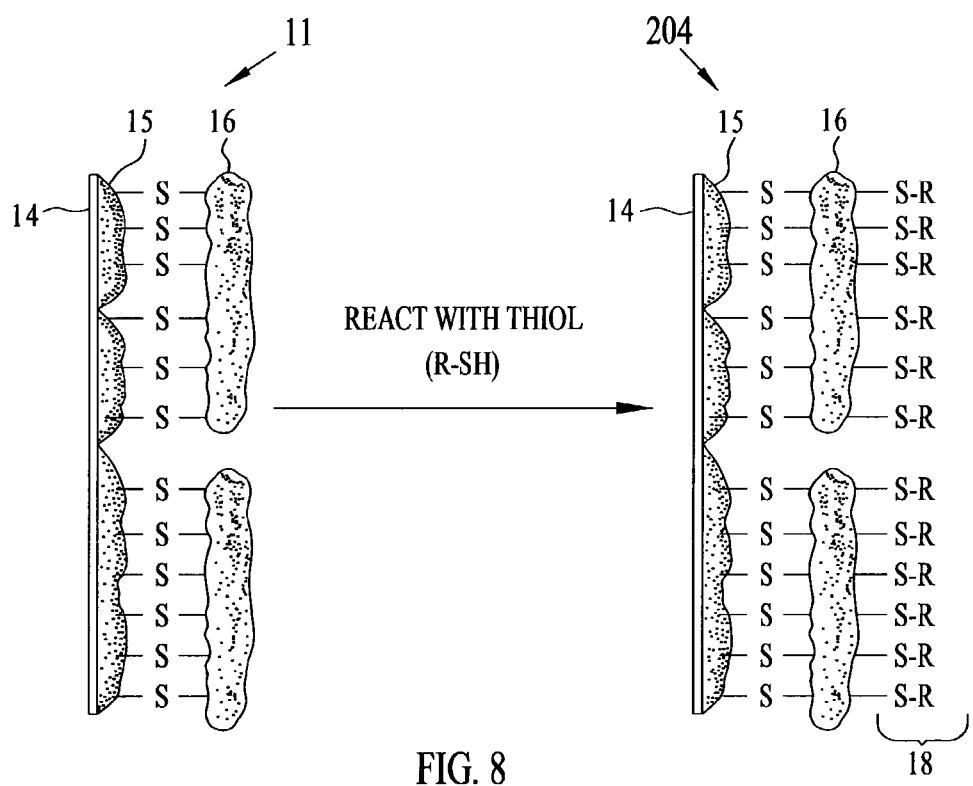
FIG. 8 shows the formation of a self-assembled monolayer (SAM) layer on the metal islands bonded to a glass substrate in the manufacture of an embodiment of a SERS chemical detection sensor.

After depositing metal islands 16 onto adhesion layer 15 a patterned metal structure 11, as shown in FIG. 8, is created. Patterned metal structure 11 may be placed in a dilute ethanolic thiol solution at ambient temperature and pressure for a period of time, such as 24 hours. While metal structure 11 is immersed in the thiol solution, metal islands 16 react with the thiol to form a durable, self-assembled monolayer 18 on the metal islands 16, as shown in FIG. 8. Thiol coatings may be selected which have an affinity for the analyte (organic compounds, metal ions, or anions) of interest. Moreover, detection limits in the ppb to ppm range are possible. TABLE 1 provides, by way of example, a list of examples of thiols and analytes that may be detected using such thiol coatings. However, TABLE 1 is not to be considered exhaustive.

TABLE 1

| Thiol Type: | Useful For Detecting: |
| --- | --- |
| 1-propanethiol | Benzene, toluene, ethylbenzene, xylene) and chlorinated solvents |
| cysteamine hydrochloride | anions such as nitrate and sulfate |
| 4-(2-pyridylazo) resorcinol modified with a disulfide group | Pb++, Cd++, and Cu++ |
| thiol derivatized dibenzo 18-crown-6 | alkali metals |

Figure 9:
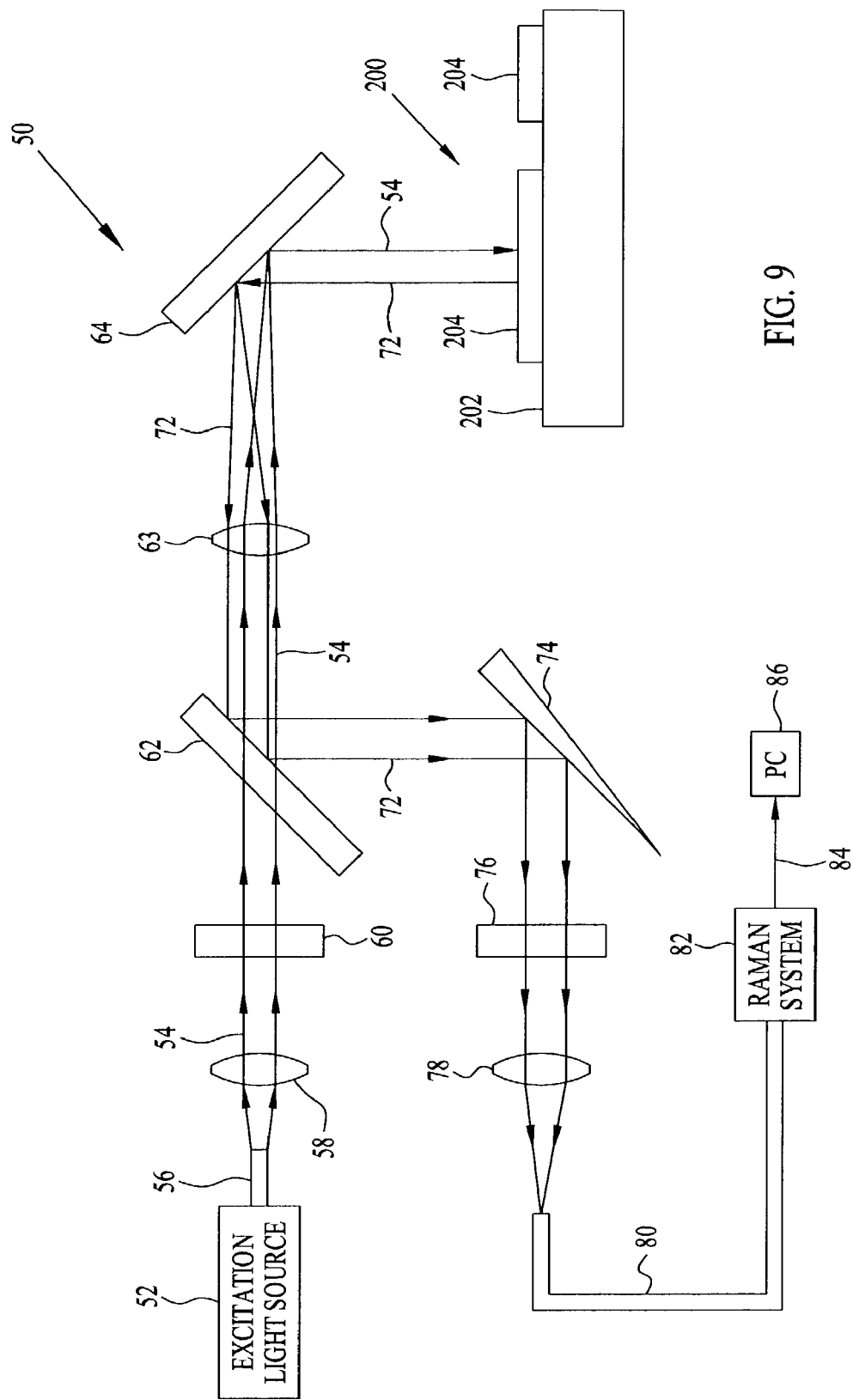
FIG. 9 shows the application of the SERS chemical detection sensor in a Raman scattering system.

An example of an application of chemical detection sensor system 200 is described with reference to FIG. 9 for obtaining Raman spectra using fiber optic system 50. Excitation light source 52, such as a Spectra Diode Laser, Inc. Model SDL-5712-H1, generates a monochromatic coherent optical signal 54 having a wavelength of 852 nm that is focused into 200 nm diameter excitation fiber 56. Optical signal 54 emitted from excitation fiber 56 is collimated by lens 58, such as a 6.4 mm focal length plano-convex lens manufactured by Newport, Model KPX010R.16. Interferences due to fiber Raman emissions may be removed by band pass filter 60 (Chroma Technology Part No. 852BP) and dichroic mirror 62 (Chroma Technology Part No. 852RDM). Excitation light 54 focused by plano-convex lens 63, having a 12.7 mm focal length, onto mirror 64 reflects excitation signal 54 to a specific SERS chemical detection sensor 204 of module 202. The interaction of excitation signal 54 and SERS chemical detection sensor 204 in the presence of an analyte of interest generally results in emission of Raman scattering signals 72 that are reflected by mirror 64 to lens 63. Scattering signals 72 reflected by mirror 74 are directed through long pass filter 76, such as a Chroma Technology, Part No. 852REF. Lens 78 focuses the scattered Raman emissions 72 into a 365 nm diameter collection optical fiber 80. Filter 76 blocks excitation signal 54, thereby preventing excitation of Raman emissions in collection fiber 80. Fiber 80 directs Raman emissions 72 to Raman system 82 which may be implemented as a Chromex Raman One Spectrometer. The Raman system 82 converts the Raman emissions 72 into a Raman spectrum 84. The Raman spectrum 84 from Raman system 82 is displayed and analyzed on a PC workstation 86.

Figure 10:
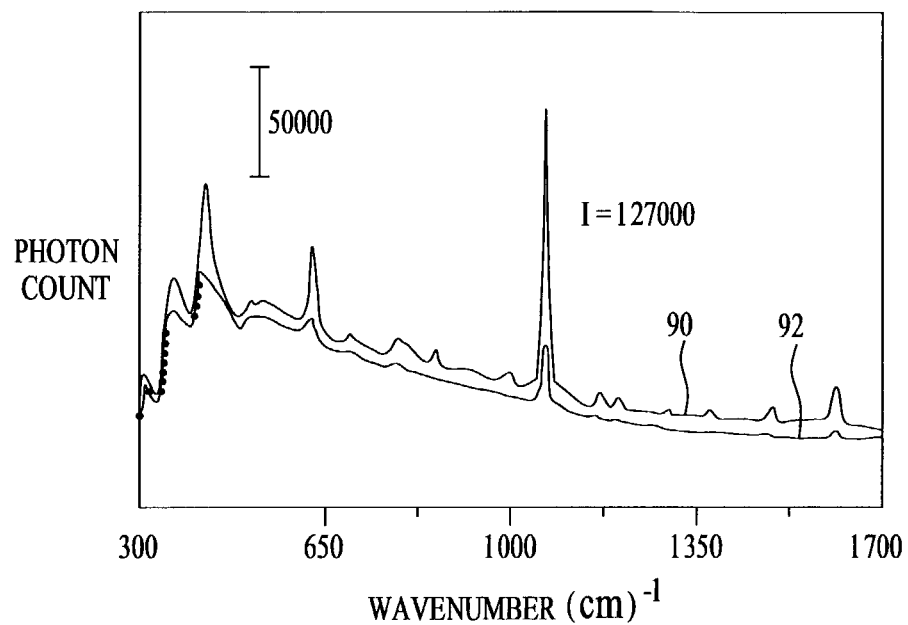
FIG. 10 shows an example of the Raman spectra of a chemical detection sensor.
Figure 11:
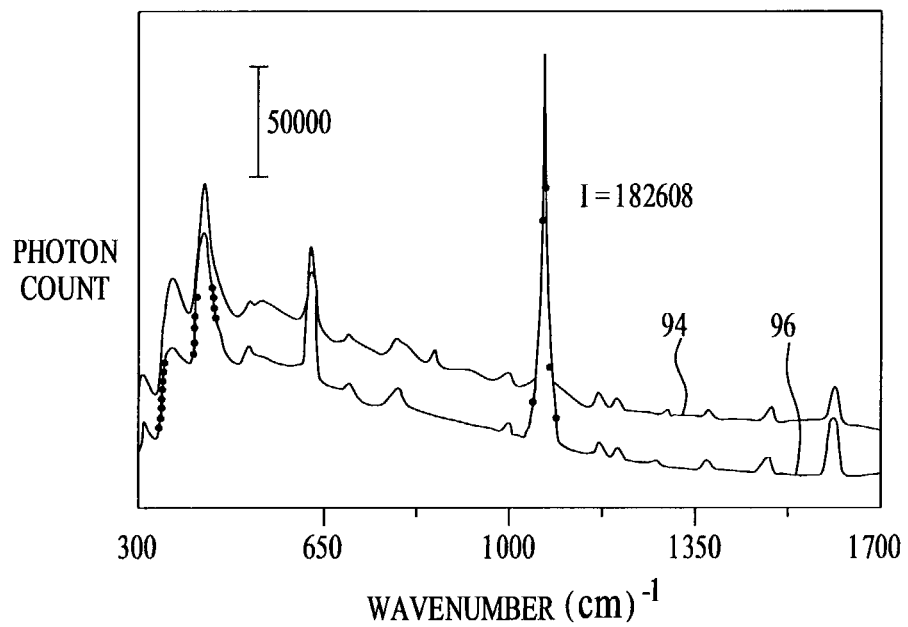
FIG. 11 shows the Raman spectra of an embodiment of a SERS chemical detection sensor.

FIGS. 10 and 11 show Raman spectra of p-thiocresol chemisorbed on a thin film of gold formed on glass substrates, referenced as a "SERS chemical detection sensor" for convenience. The horizontal axis in each of FIGS. 10 and 11 represent the wavelength of the emitted spectra. The vertical axis in each of FIGS. 10 and 11 represents optical intensity or number of photons emitted at 1073 cm$^{-1}$ detected with a Chromex Raman One Spectrometer using a diffraction grating having 600 grooves/mm and binning three horizontal pixels. The detector was operated at −50 C, and had a 100 second CCD integration time. The SERS chemical detection sensors 204 were illuminated with an 852 nm DBR diode laser. Laser power at the sample was 63 mW. The element used to generate the curves in FIG. 10 included a layer of gold having a thickness of 151 that was formed on a commercial white glass substrate. Curve 90 represents the number of photons generated from a SERS chemical detection sensor having a glass surface untreated with MCTMS. Curve 92 represents the number of photons generated from a SERS chemical detection sensor having a gold layer formed on a glass surface treated with MCTMS. Thus, from FIG. 10, it may be appreciated that a SERS chemical detection sensor comprised of a gold layer formed on commercial white glass surface that is not treated with MCTMS exhibits a good SERS response, i.e., it emits a relatively high number of photons when illuminated as described. However, the gold film has very poor adhesion to such untreated surfaces and is very fragile. Treating a commercial white glass surface with MCTMS greatly improves the durability of the bond between the gold layer and the commercial white glass surface. However, the SERS response of the MCTMS surface results in a relatively poor SERS response as revealed by curve 92 of FIG. 10.

Referring now to FIG. 11, curve 94 represents the number of photons emitted from a SERS chemical detection sensor 204 having gold islands formed on a transparent glass surface that is untreated with MCTMS and which is etched in accordance with the teachings herein. Curve 96 represents the number of photons generated from SERS chemical detection sensor 204 having gold islands 16 that is manufactured in accordance with the teachings herein. The SERS response at 1073 cm$^{-1}$ as represented by curves 94 and 96 are indistinguishable. However, the SERS chemical detection sensor used to generate curve 94 has very fragile gold islands which were not bonded well to the glass substrate, whereas the SERS chemical detection sensor 204 used to generate curve 96 has very durable gold islands. Thus, it may be appreciated that the SERS chemical detection sensors described herein each have metal islands durably bonded to a glass substrate and exhibit an excellent SERS response.

Figure 13:
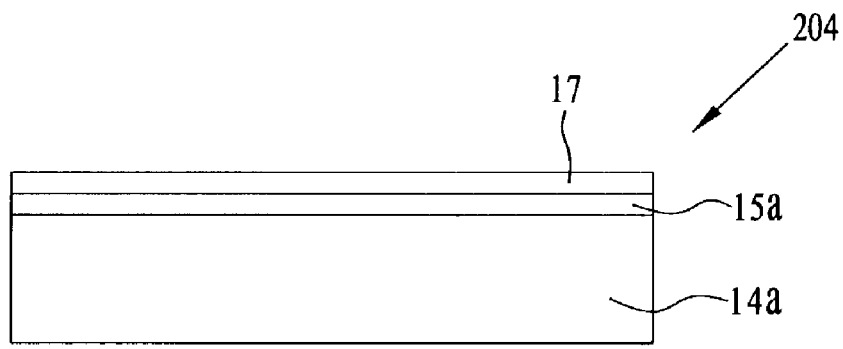
FIG. 13 is a cross-sectioned view of an embodiment of a multilayered SERS chemical detection sensor prior to electrochemical etching.

Another embodiment of a SERS chemical detection sensor 204a that exhibits a good SERS response and is durable in an aqueous environment is manufactured using electrochemical techniques described with reference to FIGS. 13–16. Referring to FIG. 13, the fabrication of SERS chemical detection sensor 204a starts by immersing substrate 14a, such as clear, borosilicate glass in a heated or boiling liquid reagent or reagents such as nitric acid, hydrofluoric acid, hydrochloric acid, or potassium hydroxide, for about 30 minutes. Such immersion removes any oils, metallic materials, and other contaminants that may be present on substrate 14a. Next, substrate 14a is removed from the boiling reagent and rinsed in either deionized or distilled water. After the water rinse, substrate 14a is immersed in hot or boiling methanol for about 30 minutes, followed by immersion in boiling acetone for about 30 minutes. This procedure removes any remaining organic contaminants. Substrate 14a then is removed from the boiling methanol and allowed to air dry, as for example, about 1 hour.

Cleaned substrate 14a then is derivitized in a silanization agent such as a 1:10 mixture by volume of (3-mercaptopropyl) trimethoxysilane (MCTMS) and ethanol for about 24 hours to form adhesion layer 15a on substrate 14a. Substrate 14a next is rinsed in ethanol to remove unreacted (3-mercaptopropyl) trimethoxysilane and allowed to air dry.

A continuous metal layer 17 made from a material such as gold, copper, or silver, is vapor deposited onto adhesion layer 15a to create a metal coated chemical detection sensor 204a. The metal coated SERS chemical detection sensor 204a next is subjected to electro chemical techniques described with reference to FIG. 14. Metal coated SERS chemical detection sensor 204a is partially immersed in an electrochemical cell 111 that includes electrolyte 101 such as a 0.1M solution of potassium chloride (KCl) held within fluid container 101 and electrodes 105 and 108, and a working electrode 113 comprised of clamp 106 and the metallic layer 17 of metal coated SERS chemical detection sensor 204a. Metal coated SERS chemical detection sensor 204a is clamped to side 102 of fluid container 104 by metallic clamp 106 so that there is electrical continuity between clamp 106 and metal layer 17. It is important that metallic clamp 106 not be immersed in the electrolyte 101 to prevent metallic ions from the clamp from contaminating the electrolyte. Also immersed in electrolyte 101 are counter electrode 105 and reference electrode 108. Counter electrode 105 preferably is made of platinum wire 107 and platinum gauze 109 that is electrically and mechanically coupled to wire 107. Electrode 105 is positioned so that gauze 109 is immersed in electrolyte 101 to increase the active surface area of electrode 105 in electrolyte 101. Reference electrode 108 preferably is made of silver/silver chloride. Electrodes 105 and 108, and clamp 106 are connected via wires 110, 112, and 114, respectively, to potentiostat 116. Potentiostat 116 maintains appropriate voltage levels at each of electrodes 105 and 108, and, electrode 113 under the supervision of computer 118 via signal line 120.

Figure 16:
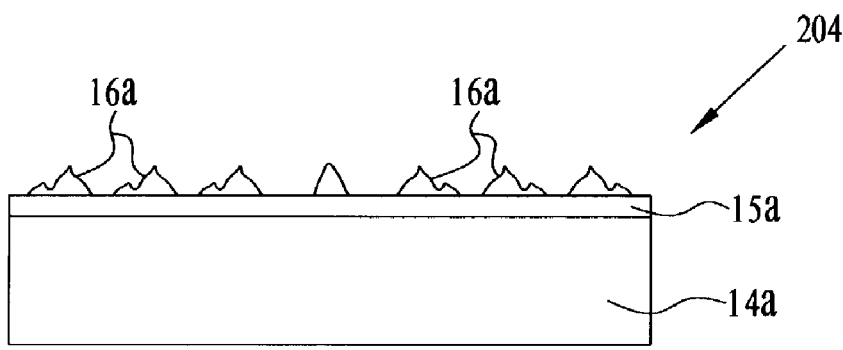
FIG. 16 is a cross-sectioned view of the multilayered SERS chemical detection sensor of FIG. 13 after the electrochemical etching.
Figure 14:
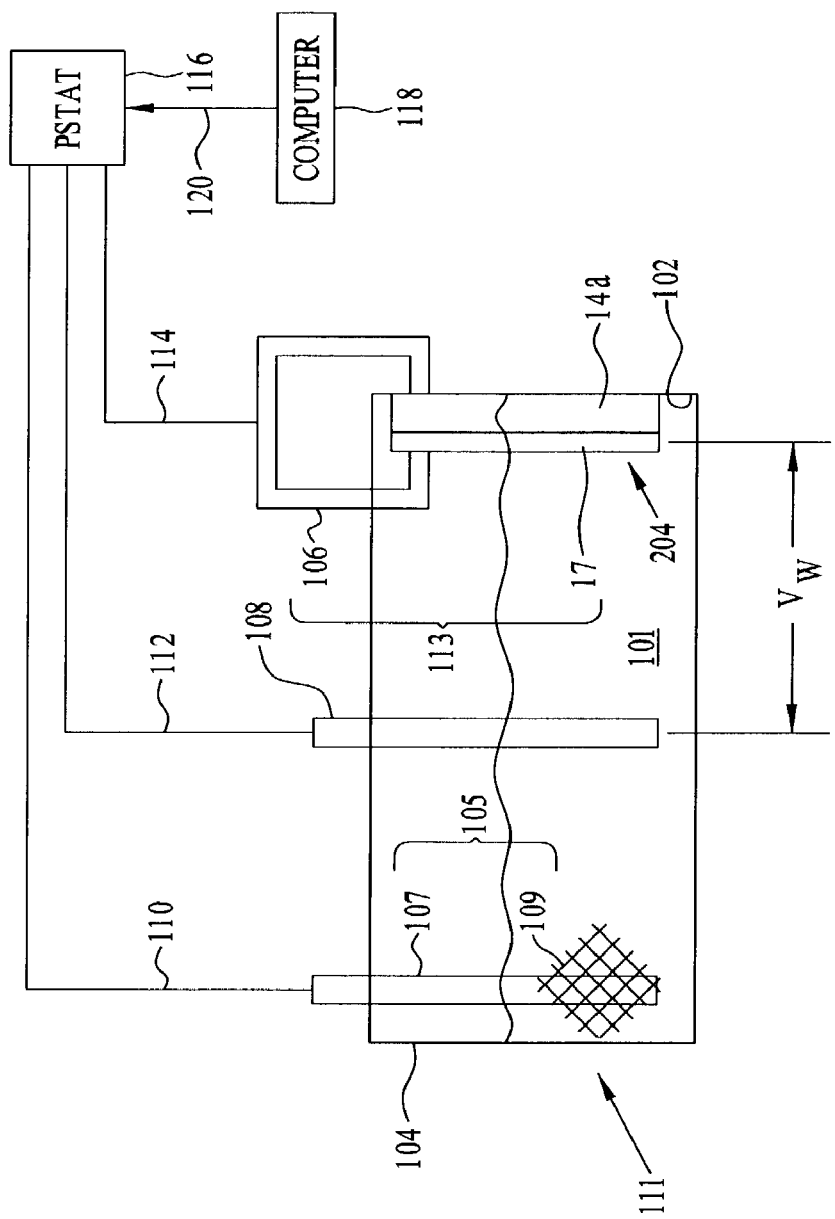
FIG. 14 shows an electrochemical cell for manufacturing an embodiment of a SERS chemical detection sensor.
Figure 15:
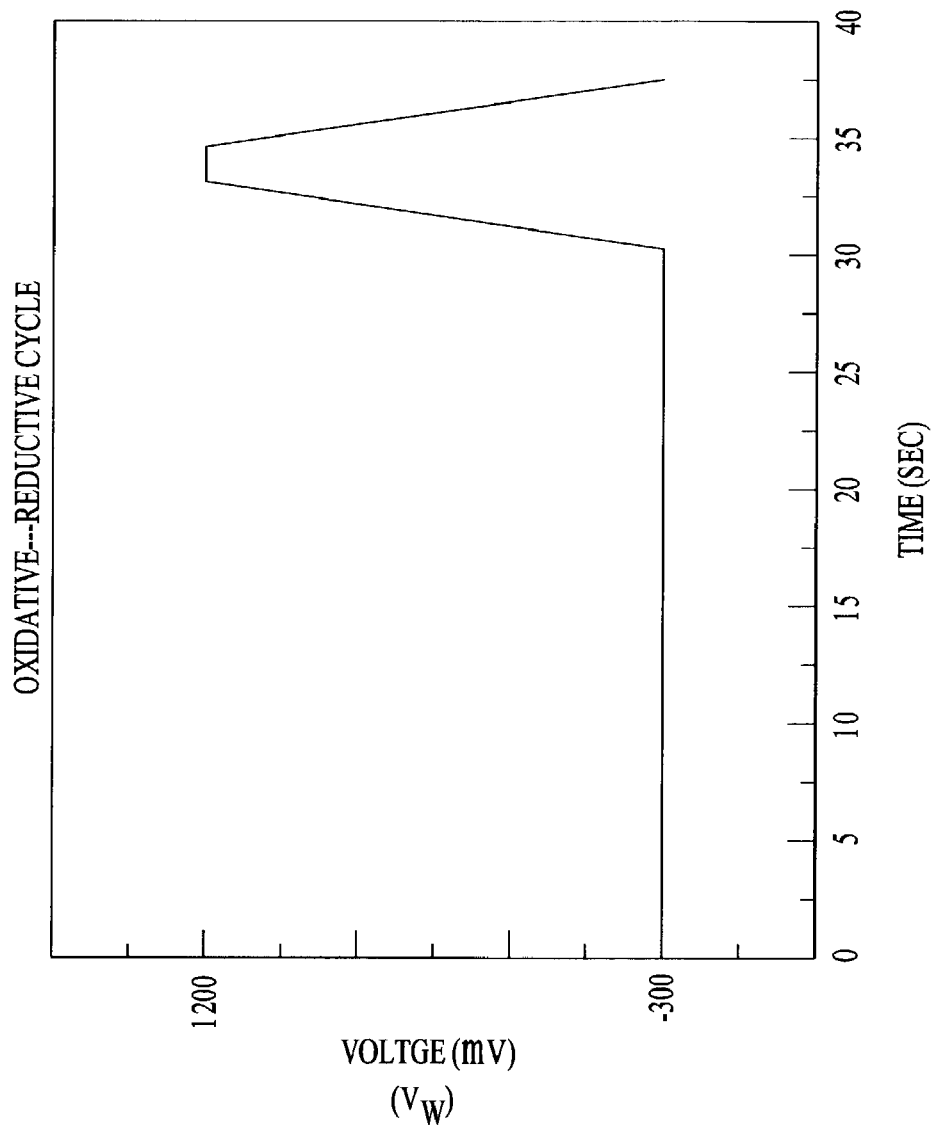
FIG. 15 is a graph representing one period of an oxidation-reduction cycle used to manufacture a SERS chemical detection sensor in the electrochemical cell of FIG. 14.

In the manufacture of SERS chemical detection sensor 204a, the voltage, $V_W$, of working electrode 113 is modulated from −300 mV to 1200 mV with respect to the voltage of reference electrode 108 for a predetermined number of oxidative-reductive cycles. An example of an oxidative-reductive cycle is shown, by way of example, in FIG. 15. Referring to FIG. 15, in an oxidative-reductive cycle, $V_W$ is held at −300 mV for about 30 seconds and then ramped to 1200 mV at a rate of about 500 mV/s. Next, $V_W$ is held at 1200 mV for about 1.3 seconds and then reduced to −300 mV at a rate of about −500 mV/s. Subjecting SERS chemical detection sensor 204a to preferably 25 oxidative-reductive cycles of the type described above with reference to FIG. 15, transforms metal layer 17 into isolated metal islands 16a having an average surface roughness of about 20 Å, thereby creating a patterned metal SERS chemical detection sensor 204a, as shown in FIG. 16.

SERS chemical detection sensor 204a then may be placed in a dilute ethanolic thiol solution at ambient temperature and pressure for a period of time, such as 24 hours, so that the metal islands 16a may react with a thiol to form a durable, self-assembled monolayer 18 on the metal islands 16. Thiol coatings may be selected which have an affinity for the analyte (organic compounds, metal ions, or anions) of interest. Examples of suitable thiol coatings are identified in TABLE 1, above.

Figure 17:
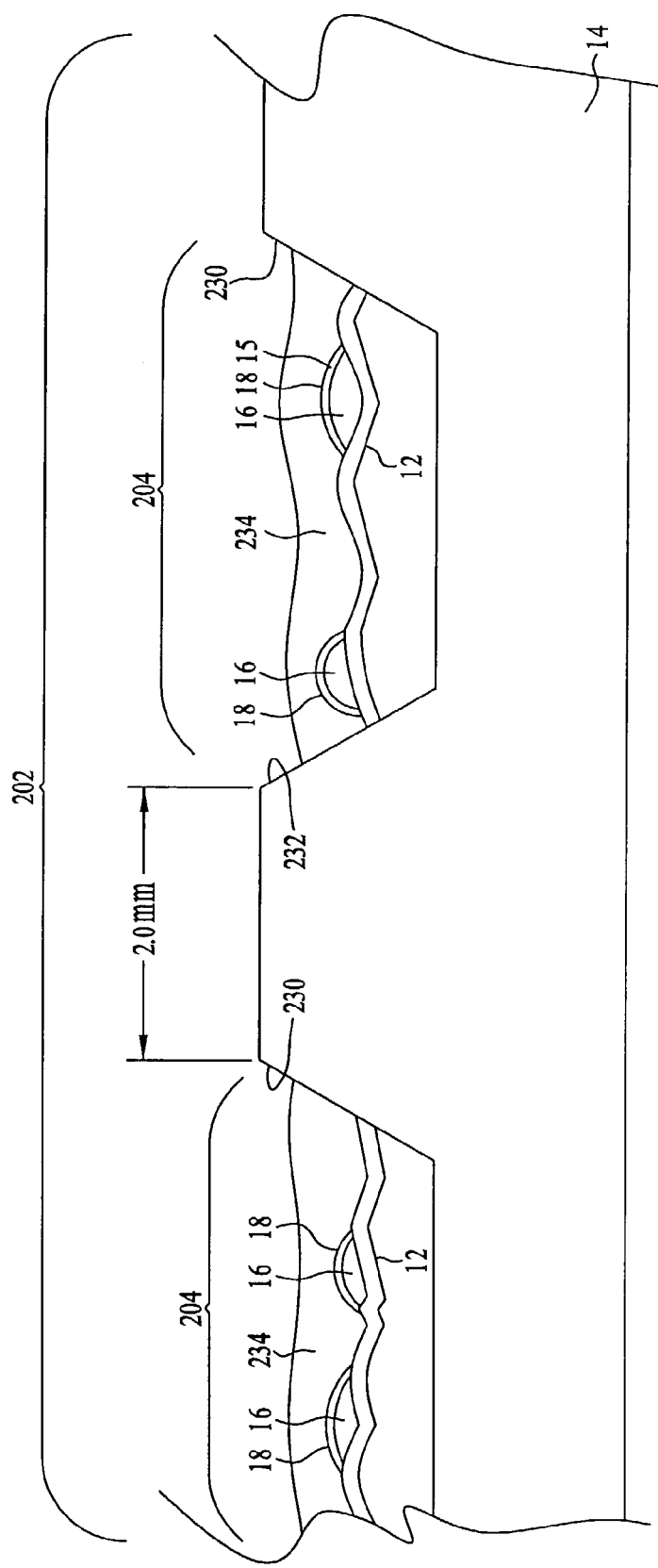
FIG. 17 shows an embodiment of a SERS chemical detection sensor system that includes SERS chemical detection sensors having a hydrogel layer.

Referring to FIG. 17, there is shown another embodiment of chemical detection sensor system 200 wherein each of the SERS chemical detection sensors 204 are fabricated in wells 230 formed in transparent substrate 14, such as borosilicate glass. By way of example, wells 230 may have 2.0 mm×2.0 mm perimeters 232 and be spaced about 2.00 mm apart in a rectangular array as shown in FIG. 3. SERS Chemical detection sensor 204 includes a specially roughened surface 12 in each well 230 of glass substrate 14. Then an adhesion layer 15 is formed over the roughened surface 12. Adhesion layer 15 promotes the bonding of the metal islands 16 to the glass substrate 14. The metal islands 16 are formed, as for example, by vapor deposition, on adhesion layer 15 to create a metal patterned substrate 11, shown in FIG. 8. A thiol coating, or self-assembled monolayer 18 on metal islands 16 protects metal islands 16 from degradation, thereby extending the lifetime of SERS chemical detection sensor 204 when exposed to air or aqueous environments from minutes or hours to months. As described above, the roughened surface 12 facilitates both a good SERS response and adhesion of the metal islands 16 to the substrate 14. Referring again to FIG. 17, a hydrogel layer 234 is formed over the self-assembled monolayer 18 and adhesion layer 15. The hydrogel layer 234 should having a thickness sufficient to completely cover the self-assembled monolayer 18, as for example, in the range of about 0.1 to 0.5 microns. The hydrogel layer 234 facilitates diffusion of an analyte towards the self-assembled monolayer of the SERS chemical detection sensor 204 and allows chemical reactions between the monolayer and analyte to occur in an aqueous environment. The hydrogel layer may contain additional reagents to facilitate the chemical reaction between the monolayer and analyte. Glass substrates having well structures suitable for use in conjunction with the disclosed embodiments may be obtained commercially from BioTrove in Cambridge, Mass.

Figure 18:
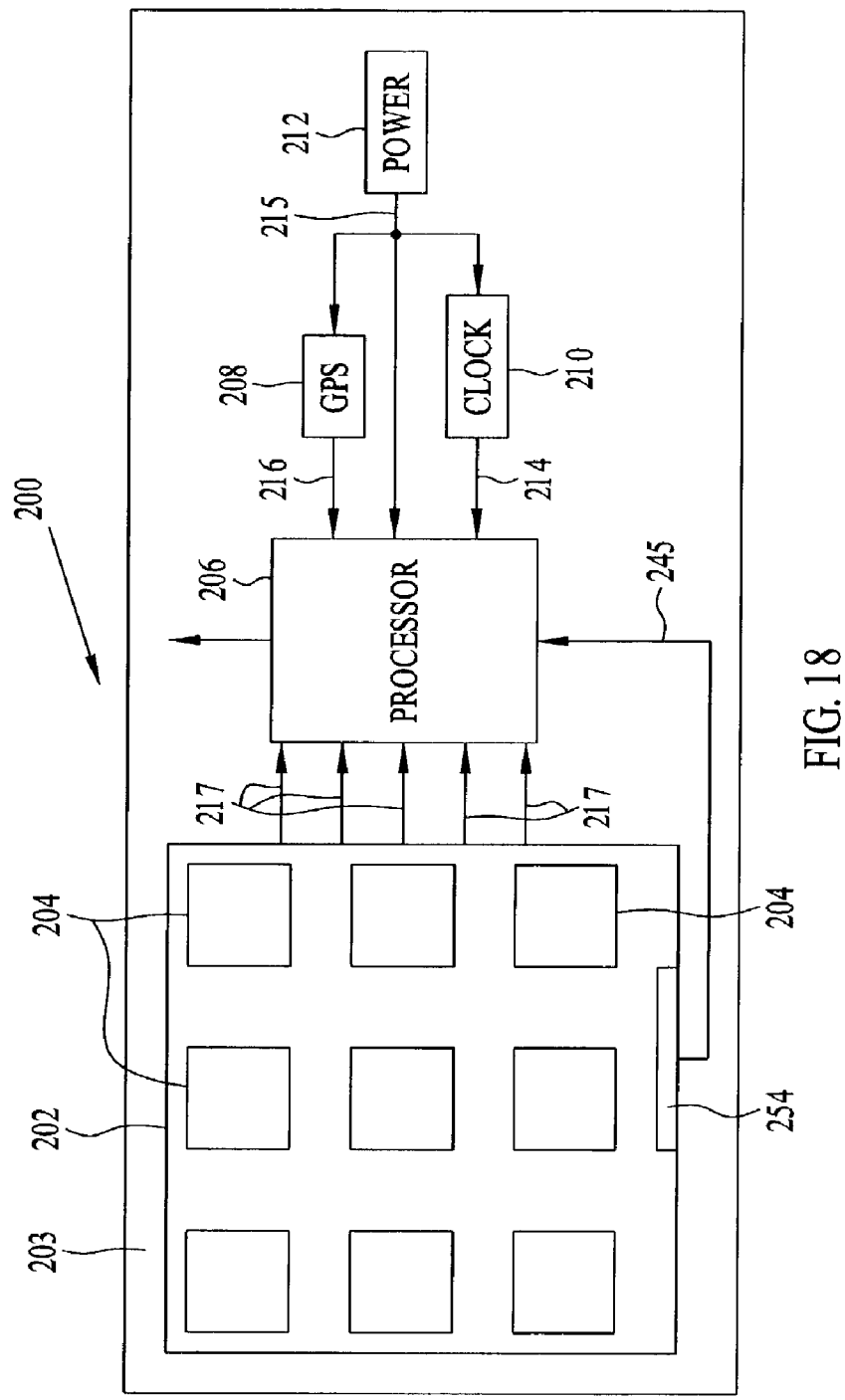
FIG. 18 shows an embodiment of a SERS chemical detection sensor system wherein each SERS chemical detection sensors includes a hydrogel layer and a pH sensor.
Figure 19:
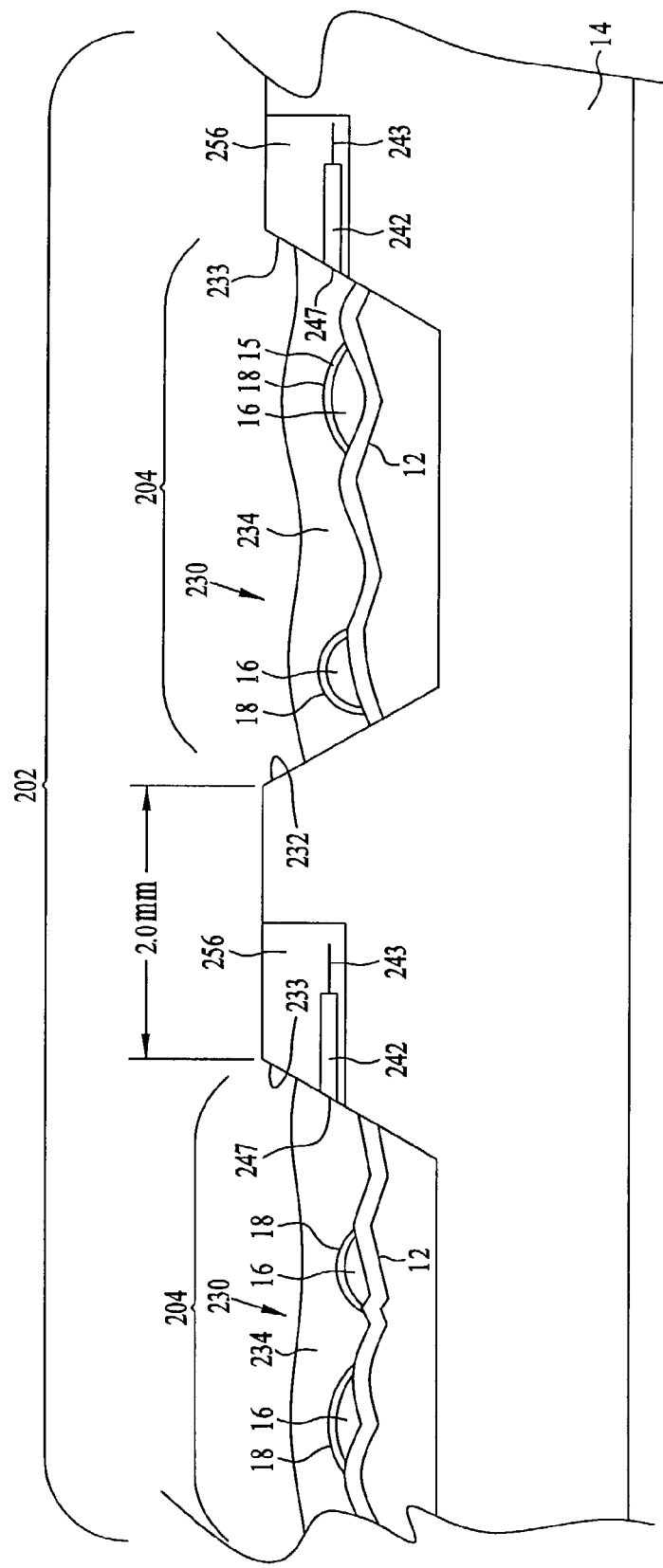
FIG. 19 is a cross-sectional view of the SERS chemical detection sensor of FIG. 18.

FIGS. 18 and 19 show an embodiment of a SERS chemical detection sensor system 200 includes a module 202 having multiple SERS chemical detection sensors 204 of which one or more may that include a pH sensor 242. The pH sensors 242 are electrically coupled via electrodes 243 to electrical interconnect 254. In turn, interconnect 254 is electrically coupled via signal line 254 to processor 206. SERS chemical detection sensors 204 of module 202 further include a hydrogel layer 234 formed in well 230 of transparent substrate 14. An end 247 of pH sensor 242 is coextensive with sidewall 233 of well 230 so that pH sensor 242 is in direct physical contact with the hydrogel layer 234. When a chemical reaction occurs at any one of SERS chemical detection sensors 204, the pH level of the hydrogel layer 234 of that particular SERS chemical detection sensor 204 changes. The occurrence of a change in the pH level of the hydrogel layers of any of pH sensors 242 is recorded by processor 206. By way of example, electrodes 243 may be fabricated from electrically conductive materials such as aluminum, silver, copper, and gold. Electrodes 243 may also be made of electrically conductive polymers. An electrical insulating layer 256, which may consist essentially of silicon dioxide, is formed over each pH sensor 242 and its associated electrodes 243 to secure and maintain the position of pH sensors 242 in the module 202. Because FIG. 19 provides an elevation view of SERS chemical detection sensor 204, only a single electrode 243 is shown associated with each SERS chemical detection sensor 204. However, it is to be understood that one or more electrodes 243 may be coextensive with side wall 233 of each SERS chemical detection sensor 204.

In another embodiment of SERS chemical detection sensor system 200, electrodes 250 may be directly coupled to processor 206, so that the processor may determine the electrical conductivity between electrodes 250 of a particular SERS chemical detection sensor 204. The electrical conductivity of hydrogel layer 234 may change when a chemical reaction occurs in any of SERS chemical detection sensors 204. Such change in the electrical conductivity may be sensed as a change of state of the conductivity of the hydro gel layer 234 by processor 204 and recorded. Generally, each of SERS chemical detection sensors 204 includes a pair of electrodes 250.

Figure 20:
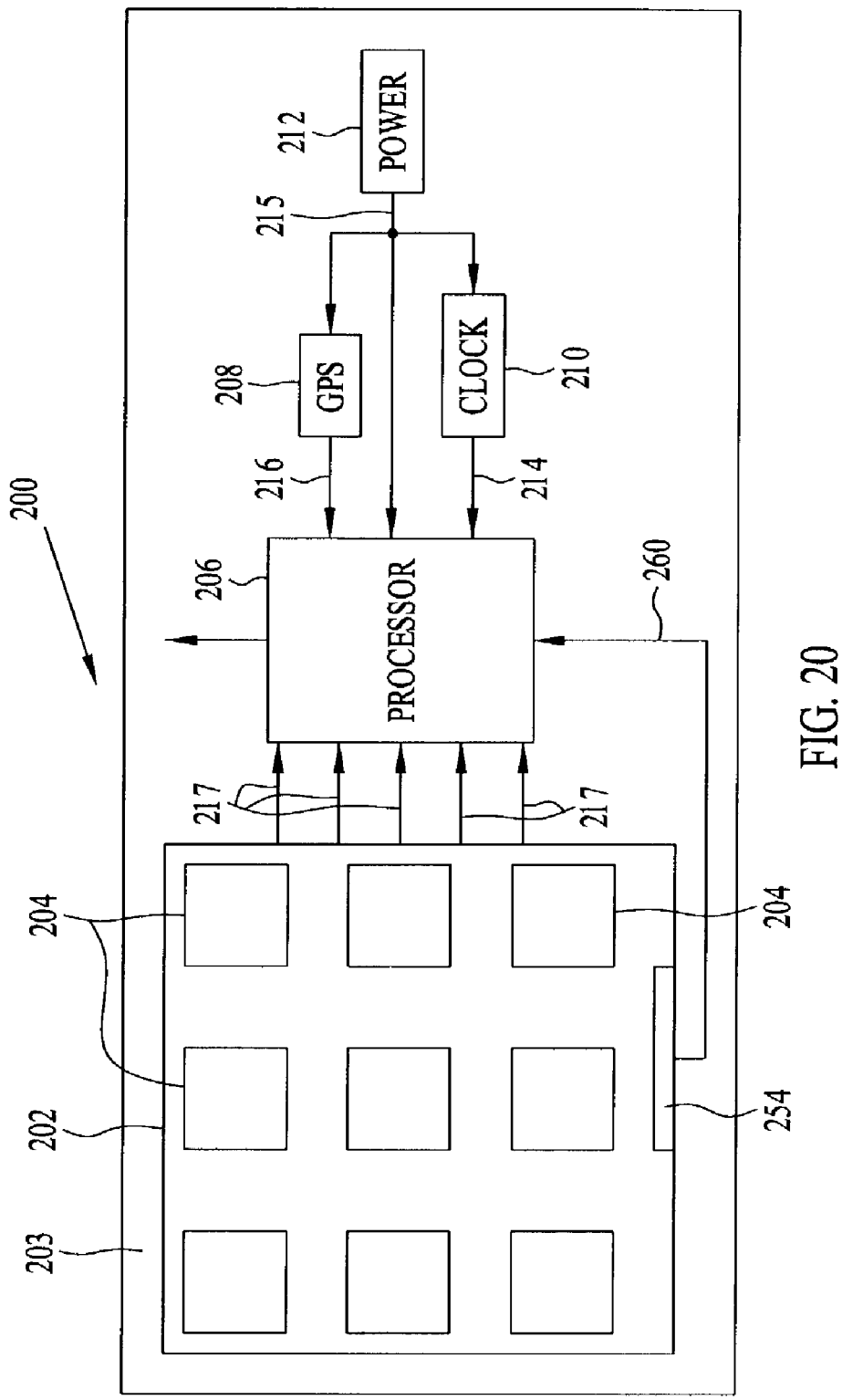
FIG. 20 shows an embodiment of a SERS chemical detection sensor system wherein each SERS chemical detection sensors includes a hydrogel layer and a thermocouple.
Figure 21:
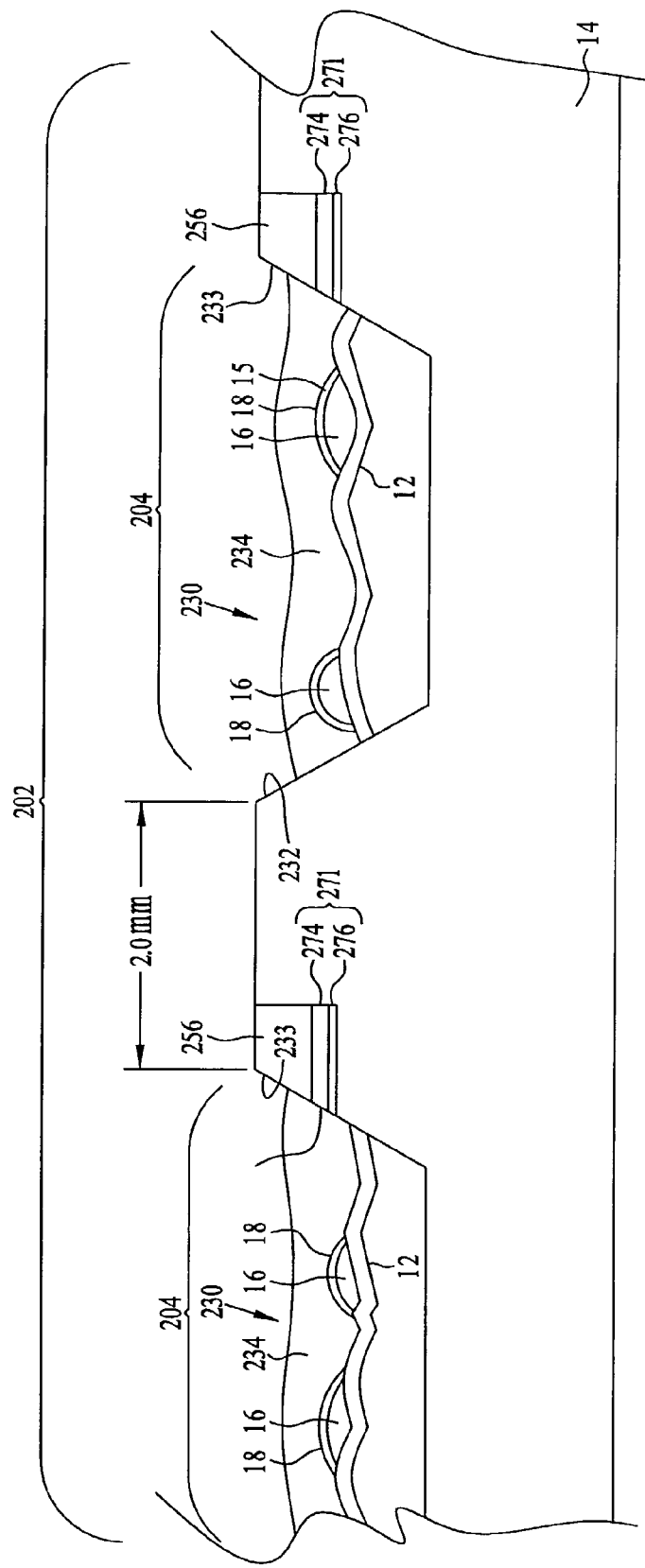
FIG. 21 is a cross-sectional view of the SERS chemical detection sensor of FIG. 20.

Another embodiment of a chemical detection sensor system 200 is shown in FIGS. 20 and 21 wherein each of SERS chemical detection sensors 204 includes a thermocouple 271 that is operably coupled through interconnect 254 to processor 206 via signal line 260. When a chemical reaction occurs at any one of SERS chemical detection sensors 204, the temperature of the hydrogel layer 234 of that particular SERS chemical detection sensor 204 changes, i.e., changes state. The temperature change is sensed by a thermocouple 272 and recorded by processor 206. Referring to FIG. 19, there is shown a cross-sectional view of SERS chemical detection sensor 204 that includes a thermocouple 271 formed on transparent substrate 14 which preferably is coextensive with the sidewall 233 of well 230 so that thermocouple 271 and the hydrogel layer 234 are in direct physical contact, thereby facilitating heat transfer from the hydrogel layer to the thermocouple. By way of example, thermocouple 271 may be fabricated from two dissimilar electrically conductive materials that define wire connects 274 and 276 that are in contact with each other at sidewall 233. An electrical insulating layer 256, which may consist essentially of silicon dioxide, is formed over thermocouples 271. Generally, the number of thermocouples 271 is cardinally related to the number of SERS chemical detection sensors 204 of module 202. From the above, it may be appreciated that pH sensors 242, electrodes 243, and thermocouple 271 all comprise elements of various types of a chemical reaction sensor 205.

Figure 22:
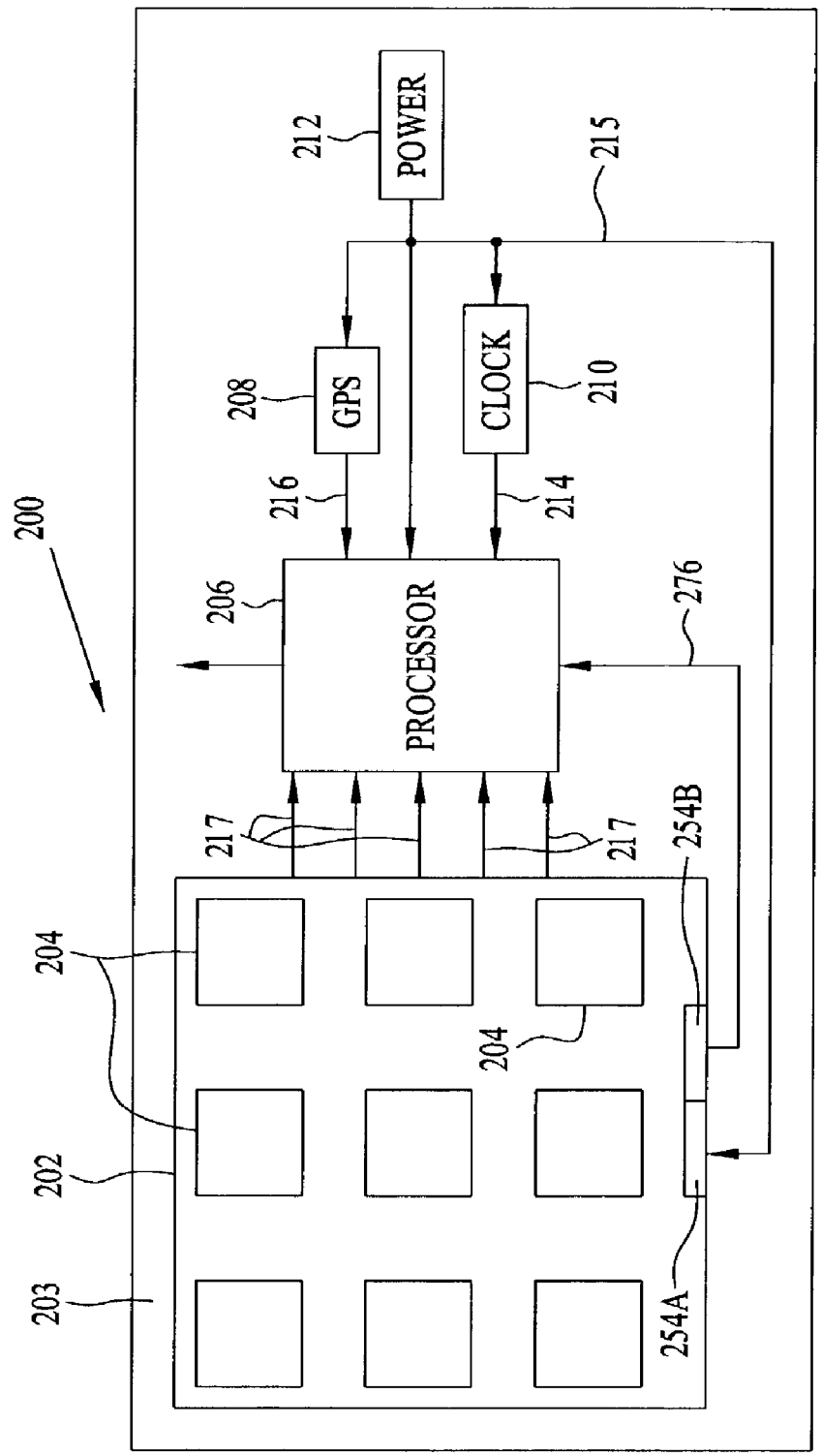
FIG. 22 shows an embodiment of a SERS chemical detection sensor system wherein each SERS chemical detection sensors includes a light emitting diode and a photodetector.
Figure 23:
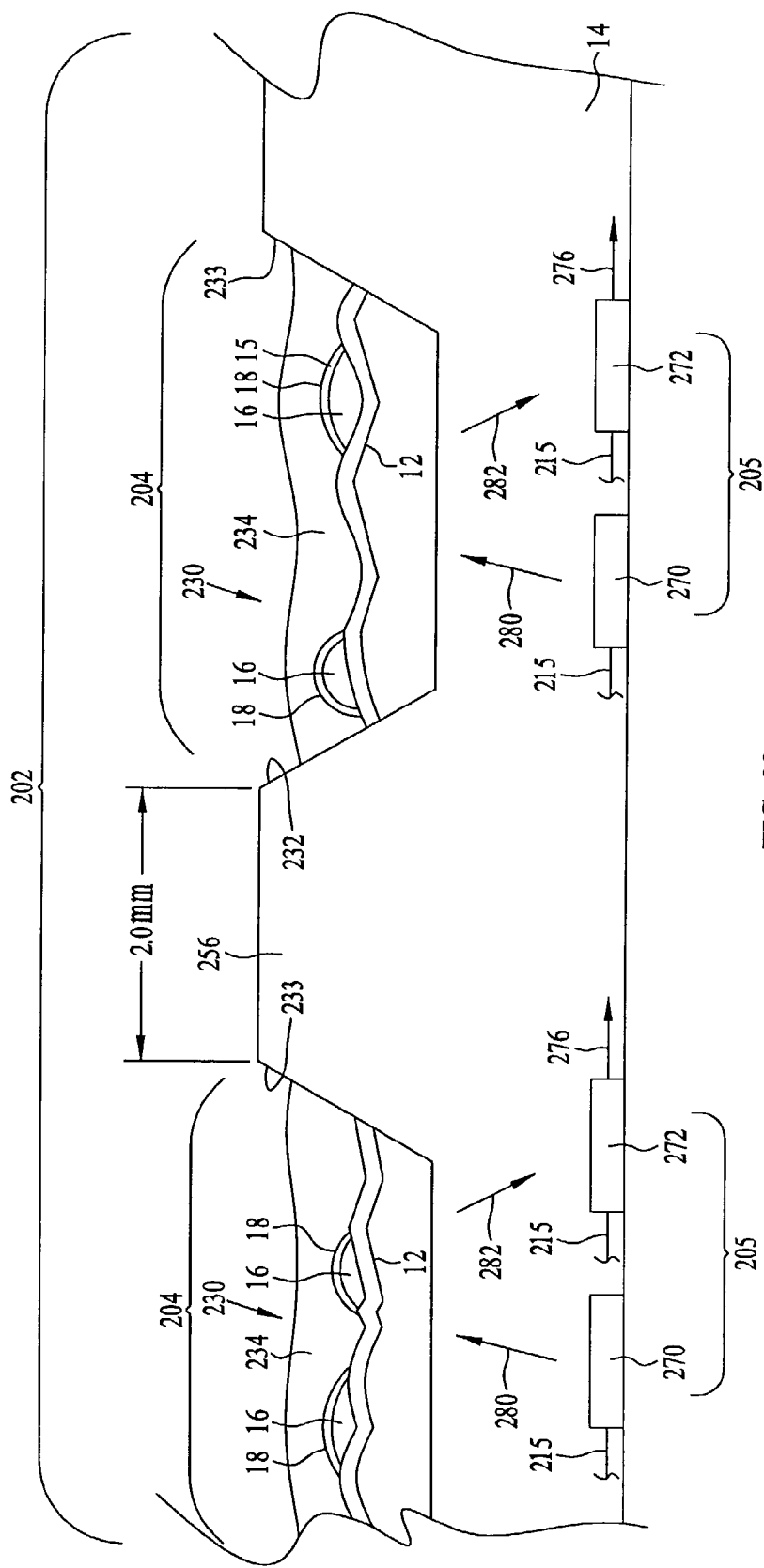
FIG. 23 is a cross-sectional view of the SERS chemical detection sensor of FIG. 22.

Another embodiment of a chemical detection sensor system 200 is shown in FIGS. 22 and 23 wherein each of SERS chemical detection sensors 204 includes a chemical reaction sensor 205 that comprises a light emitting diode (LED) 270 and photodetector 272 attached to transparent substrate 14 opposite self-assembled monolayer 18. By way of example, the light emitting diodes 270 and photodetectors 272 may be fabricated in substrate 14 using photo lithographic techniques. Electrical power to the light emitting diodes 270 and photodetectors 272 is provided by power source 212 through interconnect 254A via signal line 215. LED 270 emits an excitation light signal 280 that is directed towards self-assembled monolayer 18. When a chemical reaction occurs at any one of SERS chemical detection sensors 204, the light signal 282 that is reflected off of metal islands 16 may have different wavelength characteristics than those of excitation light signal 280. The difference in the wavelength characteristics between excitation light signal 280 and light signal 282 is believed to be due to a plasmon effect that occurs at the self-assembled monolayer. It is believed that the plasmon effect results from the change in molecular weight of the thiol that comprises the self-assembled monolayer when a chemical reaction occurs there. Photodetector 276 may be selected to be sensitive to a narrow band about the wavelength of light signal 282 that results from the occurrence of a particular chemical reaction at the self-assembled monolayer 18 of a specific chemical detection sensor 204. Upon detection of light signal 282, photodetector 276 generates a signal 276 that is provided to processor 206 via interconnect 254B. Signal 276 indicates whether photodetector 276, and hence chemical reaction sensor 205 has undergone a state change. Processor 206 then stores information that represents the occurrence of a particular type of chemical reaction at a specific chemical reaction sensor 204.

Obviously, many modifications and variations of the chemical detection sensor system described herein are possible in light of the above teachings. It is therefore to be understood that within the scope of the appended claims, the chemical detection sensor system may be practiced otherwise than as specifically described.

The invention claimed is:
1. A chemical detection sensor system, comprising:
   a support structure;
   SERS chemical detection sensors supported by said support structure, wherein each SERS chemical detection sensor is disposed to undergo a chemical reaction and a state change in the presence of an analyte;
   chemical reaction sensors, wherein each one of said chemical reaction sensors is operably coupled to one of said SERS chemical detection sensors and disposed to detect said state change;
   a processor operably coupled to said chemical reaction sensors and disposed to record said state change; and a power source disposed to energize said processor.

2. The chemical detection sensor system of claim 1 wherein each of said SERS chemical detection sensors comprises:
a glass substrate having a roughened surface;
an adhesion layer formed on said roughened surface;
metal islands formed on said adhesion layer to define a metal patterned structure; and
a self-assembled monolayer formed over said metal islands.

3. The chemical detection sensor system of claim 2 wherein metal islands consist essentially of a metal selected from the group consisting of copper, silver, and gold.

4. The chemical detection sensor system of claim 2 wherein said metal islands are formed by vapor depositing said metal on said adhesion layer.

5. The chemical detection sensor system of claim 2 wherein said self-assembled monolayer is a thiol selected from the group consisting of 1-propanethiol, cysteamine hydrochloride, 4-(2-pyridylazo) resorcinol modified with a disulfide, and thiol derivatized dibenzo 18-crown-6.

6. The chemical detection sensor system of claim 2 wherein said roughened surface has an average surface roughness that does not exceed about 2,500 Å.

7. The chemical detection sensor system of claim 2 wherein said roughened surface has an average peak-to-peak periodicity that does not exceed about 12.5 microns.

8. The chemical detection sensor system of claim 2 wherein said roughened surface has an average surface roughness that does not exceed about 2,500 Å and an average peak-to-peak periodicity that does not exceed about 12.5 microns.

9. The chemical detection sensor system of claim 2 further including a hydrogel layer formed over said self-assembled monolayer.

10. The chemical detection sensor system of claim 9 wherein said chemical reaction sensor is selected from the group consisting of a pH sensor, surface acoustic wave device, thermocouple, and electrical conductivity sensor.

11. The chemical detection sensor system of claim 1 further comprising:
a clock disposed to generate a clock signal representing a time value; and
wherein said processor is disposed to record said time value when said processor records said data.

12. The chemical detection sensor system of claim 1 further comprising:
a global positioning system disposed to generate a global positioning signal representing a global position value; and wherein said processor is disposed to record said global position value when said processor records said data.

13. A chemical detection sensor system sensor, comprising:
a support structure;
SERS chemical detection sensors supported by said support structure, wherein each SERS chemical detection sensor is disposed for undergoing a chemical reaction and a state change in the presence of an analyte;
chemical reaction sensors, wherein each one of said chemical reaction sensors is operably coupled to one of said SERS chemical detection sensors and disposed to detect said state change;
a clock disposed to generate a clock signal representing a time value;
a global positioning system disposed to generate a global positioning signal representing a global position value;
a processor operably coupled to said chemical reaction sensors and disposed to record said time value, said global position value and data representing said state change; and
a power source disposed to energize said processor.

14. The chemical detection sensor system of claim 13 wherein each of said SERS chemical detection sensors comprises:
a glass substrate having a roughened surface;
an adhesion layer formed on said roughened surface;
metal islands formed on said adhesion layer to define a metal patterned structure; and
a self-assembled monolayer formed over said metal islands.

15. The chemical detection sensor system of claim 14 wherein metal islands consist essentially of a metal selected from the group consisting of copper, silver, and gold.

16. The chemical detection sensor system of claim 14 wherein said metal islands are formed by vapor depositing said metal on said adhesion layer.

17. The chemical detection sensor system of claim 14 wherein said self-assembled monolayer is a thiol selected from the group consisting of 1-propanethiol, cysteamine hydrochloride, 4-(2-pyridylazo) resorcinol modified with a disulfide, and thiol derivatized dibenzo 18-crown-6.

18. The chemical detection sensor system of claim 14 wherein said roughened surface has an average surface roughness that does not exceed about 2,500 Å.

19. The chemical detection sensor system of claim 14 wherein said roughened surface has an average peak-to-peak periodicity that does not exceed about 12.5 microns.

20. The chemical detection sensor system of claim 14 wherein said roughened surface has an average surface roughness that does not exceed about 2,500 Å and an average peak-to-peak periodicity that does not exceed about 12.5 microns.

21. The chemical detection sensor system of claim 14 further including a hydrogel layer formed over said self-assembled monolayer.

22. The chemical detection sensor system of claim 21 wherein said chemical reaction sensor is selected from the group consisting of a pH sensor, surface acoustic wave device, thermocouple, and electrical conductivity sensor.

23. A chemical detection sensor system, comprising:
a support structure;
SERS chemical detection sensors supported by said support structure, wherein each of said SERS chemical detection sensors is disposed to undergo a chemical reaction and a state change in the presence of an analyte, and comprises:
a transparent substrate having a roughened surface;
an adhesion layer formed on said roughened surface;
metal islands formed on said adhesion layer to define a metal patterned structure; and
a self-assembled monolayer formed over said metal islands;
chemical reaction sensors, each one comprising a light emitting diode and a photodetector affixed to said transparent substrate opposite said self-assembled monolayer, wherein each one of said chemical reaction sensors is operably coupled to one of said SERS chemical detection sensors and disposed to detect said state change;
a processor operably coupled to said chemical reaction sensors and disposed to record data representing said state change; and
a power source disposed to energize said processor and said chemical reaction sensors.

* * * * *